(12) United States Patent
Buss et al.

(10) Patent No.: US 11,896,528 B2
(45) Date of Patent: Feb. 13, 2024

(54) SCANNING LASER OPHTHALMIC TREATMENT SYSTEM AND METHOD OF OPERATION

(71) Applicant: Norlase ApS, Ballerup (DK)

(72) Inventors: Thomas Buss, Ballerup (DK); Greg Fava, Redwood City, CA (US); Mariafernanda Vilera Suárez, Ballerup (DK); Peter Skovgaard, Birkerød (DK)

(73) Assignee: NORLASE ApS, Ballerup (DK)

( * ) Notice: Subject to any disclaimer, the term of this patent is extended or adjusted under 35 U.S.C. 154(b) by 44 days.

(21) Appl. No.: 16/994,722

(22) Filed: Aug. 17, 2020

(65) Prior Publication Data

US 2021/0100688 A1 Apr. 8, 2021

Related U.S. Application Data

(60) Provisional application No. 62/887,258, filed on Aug. 15, 2019.

(51) Int. Cl.
*A61F 9/008* (2006.01)

(52) U.S. Cl.
CPC ...... *A61F 9/00823* (2013.01); *A61F 2009/00863* (2013.01); *A61F 2009/00885* (2013.01); *A61F 2009/00897* (2013.01)

(58) Field of Classification Search
CPC ........ A61F 9/00823; A61F 2009/00863; A61F 2009/00885; A61F 2009/00897;
(Continued)

(56) References Cited

U.S. PATENT DOCUMENTS 7,766,903 B2 8/2010 Blumenkranz et al.
7,940,439 B2 5/2011 Jung et al.
(Continued)

FOREIGN PATENT DOCUMENTS

DE 102008012826 A1 10/2008
DE 102008013116 A1 10/2008
(Continued)

OTHER PUBLICATIONS

"Bragg mirror (reflector) features and technologies, Jul. 15, 2016, Optromix, https://fibergratings.com/bragg-mirror-reflector-features-and-technologies/" (Year: 2016).*
(Continued)

*Primary Examiner* — Joseph M Dietrich
*Assistant Examiner* — Michael T. Holtzclaw
(74) *Attorney, Agent, or Firm* — HoustonHogle LLP

(57) ABSTRACT

An ophthalmic laser treatment delivers patterned laser energy to an eye of a patient. A pattern-scanning laser device of the laser treatment system includes a laser module, a scanning module and delivery optics. The laser module generates laser energy (e.g. via a green laser diode), which is directed to the scanning module via a fiber optic cable. The scanning module produces the patterned laser energy by reflecting the laser energy into the delivery optics at different angles via a dielectric MEMS scanning mirror. The delivery optics includes an F-theta lens, a motorized and wirelessly-controlled spot-size selector module, and a focusing lens. A mobile computing device receives parameter information via a graphical user interface or voice control and sends the parameter information to the pattern-scanning laser device. In response to receiving activation signals from an activation unit, the pattern-scanning laser device emits the patterned laser energy based on the parameter information.

14 Claims, 13 Drawing Sheets

(58) Field of Classification Search
CPC ....... A61F 2009/00891; A61F 9/00821; G02B 27/48; G02B 26/10; G02B 26/105
See application file for complete search history.

(56) References Cited

U.S. PATENT DOCUMENTS

| | | | |
|---|---|---|---|
| 8,670,474 | B2 | 3/2014 | Jensen et al. |
| 9,685,755 | B2 | 6/2017 | Bjarlin et al. |
| 10,179,071 | B2* | 1/2019 | Mordaunt ............ A61F 9/00821 |
| 2008/0015553 | A1* | 1/2008 | Zacharias ................ A61F 9/008 606/4 |
| 2011/0245817 | A1* | 10/2011 | Yokosuka ............ A61F 9/00821 606/4 |
| 2011/0319874 | A1* | 12/2011 | Mintz .................. A61F 9/00802 606/4 |
| 2013/0103008 | A1* | 4/2013 | Sramek ............... A61F 9/00821 606/4 |
| 2013/0204235 | A1* | 8/2013 | Palanker ................. A61F 9/008 606/4 |
| 2014/0324031 | A1* | 10/2014 | Abe ......................... A61F 9/008 606/4 |
| 2015/0202083 | A1* | 7/2015 | Takeda ................... A61B 18/20 606/4 |
| 2015/0366713 | A1* | 12/2015 | Shazly ................ A61F 9/00821 606/5 |
| 2018/0110651 | A1* | 4/2018 | Gonzalez ................. A61F 9/008 |
| 2019/0019514 | A1 | 1/2019 | Fava et al. |

FOREIGN PATENT DOCUMENTS

| | | |
|---|---|---|
| DE | 102008064772 B3 | 5/2018 |
| WO | WO2015091353 A1 | 6/2015 |
| WO | WO2017167657 A1 | 10/2017 |
| WO | WO2018146070 A2 | 8/2018 |

OTHER PUBLICATIONS

"Jonathan Ehrmann, Optics for vector scanning, Feb. 1, 1991, Proceedings of SPIE, pp. 245-255, https://www.spiedigitallibrary.org/conference-proceedings-of-spie/1454/0000/Optics-for-vector-scanning/10.1117/12.28036.full" (Year: 1991).*

"Surbhi S, Difference Between Convex and Concave Lens, Dec. 8, 2018, Key Differences, https://keydifferences.com/difference-between-convex-and-concave-lens.html" (Year: 2018).*

Anonymous, "Micro-Scanning Mirrors for High-Power Applications in Laser Surgery," Fraunhofer Institute for Photonic Microsystems IPMS, 1-2 ( ).

Sandner, T., et al., "Micro-Scanning Mirrors for High-Power Laser Applications in Laser Surgery," Lane 2014, 1-10 (2014).

Sandner, T., et al., "Highly Reflective Optical Coatings for High Power Applications of Micro Scanning Mirrors in the UV-VIS-NIR Spectral Region," MOEMS Display, Imaging, Miniaturized Microsystems IV, 61140H-1-61140H-15 (2006).

Schroedter, R., et al., "Microcontroller Based Closed-Loop Control of a 2D Quasi-Static/Resonant Microscanner with On-Chip Piezo-Resistive Sensor Feedback," MOEMS and Miniaturized Microsystems XVI, 1011605-1-1011605-11 (2017).

* cited by examiner

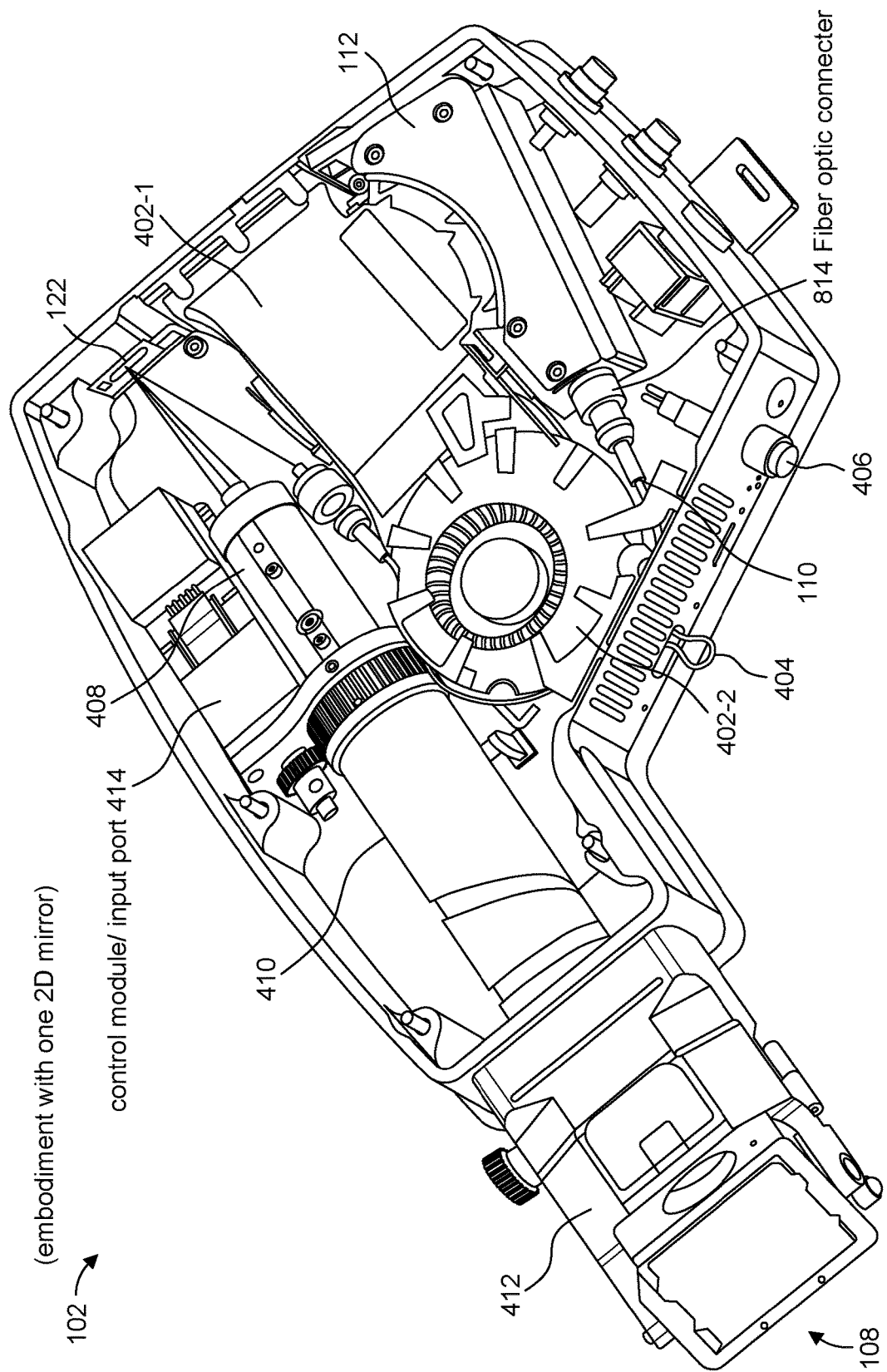

SCANNING LASER OPHTHALMIC TREATMENT SYSTEM AND METHOD OF OPERATION

RELATED APPLICATIONS

This application claims the benefit under 35 USC 119(e) of U.S. Provisional Application No. 62/887,258, filed on Aug. 15, 2019, which is incorporated herein by reference in its entirety.

BACKGROUND OF THE INVENTION

Laser-based treatment, such as laser photocoagulation, is a well-established practice within ophthalmology for treating diseases such as glaucoma, diabetic retinopathy, wet age-related macular degeneration (AMD), and other retinal diseases.

Laser coagulation requires the exposure of the retina to visible laser light and relies on the selective absorption in melanin and hemoglobin (at a wavelength range of 514-577 nanometers (nm)) to achieve coagulation. Laser photocoagulators focus on this range of wavelengths and aim to provide small spot sizes (typically 50 to 500 micrometers ($\mu m$)), adjustable power (0-3.0 Watts (W)) and long depth of focus to increase treatment precision and ease of use. In the course of treatments, doctors will regularly set and update parameters dictating the laser energy to be delivered. These parameters can include power, pulse duration, and repeat interval, among other examples. Common laser photocoagulator use now includes shorter pulse durations of 50 microseconds ($\mu sec$) to 50 milliseconds (msec) to limit the amount of damage at the target tissue and spare adjacent tissues from any thermal injury.

Commonly, slit lamps are used for delivering the laser energy to the patient's eye. In these systems, the patients sit up in an examination chair, rest their chin on a chin rest, and place their forehead against a forehead band, both of which keep the patient's head in place during the procedure.

Another common device is a Laser Indirect Ophthalmoscope (LIO), which is a head mounted device, worn by the doctor to deliver laser energy into a patient's eye. During procedures using the LIO, the doctor moves the laser console for generating the laser energy, which is positioned on a cart or table, to be in the proximity of the patient who is usually in a supine position. The doctor then walks around the patient to deliver the laser energy to the desired portions of the retina.

The conventional laser photocoagulation treatment is single-spot photocoagulation, which uses a single application of laser energy, usually applied for 100-200 msec. Despite the effectiveness of conventional single-spot retinal photocoagulation, it remains an uncomfortable experience for the patient, and the treatment can have side effects such as loss of vision, loss of contrast and color perception or more severe reactions such as a rupture of bruchs membrane, tractional retinal detachments or accidental exposure of the Fovea.

In recent years, multi-spot, pattern-scanning photocoagulation has gained further significance and has improved the safety and efficiency of laser photocoagulation. In pattern-scanning photocoagulation, laser spots are applied in a series of configurable patterns or arrangements. Customized and pre-configured patterns can be selected to match underlying disease to be treated. As an example, arrays of 2×2 (4 spots) to 5×5 (25 spots) are useful in efficiently treating large areas of the retina during pan retinal photocoagulation (PRP) while circles of different diameters are useful in encapsulating a retinal tear or hole. To start a procedure the doctor would titrate the power and duration with a single spot to accurately gauge the parameters needed for a particular patient. The doctor then selects the desired pattern and positions the pattern on the targeted area. In addition to regular laser photocoagulation therapeutic benefits, such as preventing growth of unwanted blood vessels and fixating the retina, and lowering the prevalence of vision impairment, multi-spot photocoagulation is significantly (5-10 times) faster than single-spot treatment. Due to a shorter exposure time (10-20 msec), multi-spot photocoagulation treatment also causes lesser collateral damage such as thermal diffusion into the choroid, resulting in a treatment that is less painful to the patient. Less pain to the patient and faster pattern delivery enables single session treatment that used to be split up into two or more treatment sessions with conventional photocoagulation.

Current pattern scanning lasers utilize a computer and galvanometer drivers to instruct the positioning of each galvanometer to the desired pattern display selected on the user interface. These systems typically use mirrors mounted on galvanometers placed into a location that facilitates accurate delivery into a patient's eye. The laser light is coupled into an optical fiber to bring the laser light to the delivery module. There, the laser light is sent to two sequential galvanometer (X & Y Axis) configurations, which generate a two-dimensional pattern by quickly steering the laser beam and automatically delivering all laser pulses in the selected pattern. An optical system (zoom telescope or discrete fiber/optics manipulation) is required to adjust the spot-size ($50\mu$-$500\mu$). All of this is integrated into a workstation including a slit-lamp used to illuminate and visualize the target tissue.

SUMMARY OF THE INVENTION

Conventional pattern-scanning laser treatment systems have some disadvantages, including a large physical footprint, low reliability due to complex electronics and galvanometers, and prohibitive cost. Moreover, some current systems cannot be used with a doctor's existing slit lamp.

Today, doctors are required to either purchase a slit-lamp with an integrated pattern-scanning laser treatment system or an add-on version for an existing slit-lamp, in which case the doctor must place a bulky laser box and electronic drivers next to their slit-lamp impeding on patient/doctor space. In either case, the systems have a high initial cost partially due to computerized control systems and the high cost of precision galvanometers. Furthermore, the add-on versions include external fiber optic cables, which are vulnerable and might require service, increasing the ongoing maintenance costs for these systems. Due to these costs, multi-spot laser treatment is sometimes out of reach for many doctors.

For doctors that do provide multi-spot laser treatment, the pattern-scanning laser treatment systems also tend to occupy valuable workspace in an ophthalmic practice, especially around surgery tables and in small treatment lanes. The galvanometers for delivering the patterned laser energy are generally expensive and prone to outside electronic interferences which can lead to distortion or noise noticeable in viewing a pattern. Systems that are integrated into slit-lamps make it difficult or impossible for doctors to use the slit-lamps for non-laser procedures, while the add-on systems cannot be moved easily due to their large size, weight and fragility. As a result, doctors typically have laser-dedicated rooms, tables and slit-lamps, further increasing overhead.

Furthermore, many systems have ineffective and inefficient user interfaces.

Interfaces based on physical buttons make it impossible to adapt the controls to changing parameters and treatment protocols. In many cases, doctors only use a small subset of available patterns, commonly using the 2×2 and 3×3 options, which are currently manually achieved or achieved via overly complex user interfaces.

Cost of these systems to the ophthalmic market is usually 3 to 5 times more expensive than a single spot laser photocoagulator, limiting its use to higher volume offices and clinics.

As a result of these disadvantages, a relatively small proportion of doctors have a pattern-scanning laser treatment system at their disposal.

Thus, a need exists for a pattern-scanning laser treatment system that is affordable, efficient, compact, flexible, and intuitive for users.

At the same time, higher power diode lasers are currently in development. In one example, the lasers produce laser energy in the therapeutic wavelength for visible green light (e.g. 520 nm) with an output power of 1.3 Watts, and similar green diode lasers with even higher output powers are anticipated as the technology continues to mature. In this vein, these higher-power direct diode lasers can be used to decrease the size and complexity of the laser module and at the same time increasing its efficiency.

The presently disclosed scanning laser device combines one or more compact direct diode lasers with MicroElectroMechanical System (MEMS) scanning mirrors and advanced delivery optics, all enclosed within a compact assembly. The laser module produces laser energy, which is directed via a fiber optic cable to the scanning module, which reflects the patterned laser energy into the delivery optics to the target tissue.

The size and weight reduction resulting from the use of the high power laser diode and compact MEMS technology is significant. This reduced footprint allows the pattern-scanning laser device to be easily mounted to a doctor's existing slit-lamp by utilizing overhead space of the slit lamp and eliminating the external fiber cable, thus enabling the slit-lamp to remain usable for other treatments despite the laser source being mounted and increasing reliability and reducing downtime. The system would also enable easy transport to other offices or treatment lanes. In another embodiment, the pattern-scanning laser device is fully integrated into a slit-lamp, which would be much less bulky than current fully integrated pattern-scanning lasers. In yet other embodiments, the pattern-scanning laser device can be an add-on device to an LIO or microscope adapter, among other examples.

Additionally, a tablet mobile computing device provides a graphical user interface and/or voice control functionality for specifying parameters which are wirelessly sent to the scanning laser device. This physical decoupling of the laser source from the control interface allows even greater flexibility in the configuration of the laser system within the treatment space.

The simpler design of the scanning laser also reduces costs relative to existing systems. For example, the laser requires fewer components and benefits significantly from semiconductor scale economies. The MEMS scanning mirror(s) is also simpler, compared to competing solutions using 1, 2 or 3 galvanometers and multiple optical fibers (e.g. one fiber per spot size). The scanning mirror chips have compact dimensions of only a few millimeters each and are inexpensive to manufacture compared to other pattern scanning solutions. The scanning laser device can include a cooling mechanism such as a baffle adjacent to the laser module and/or a fan to provide cooling. Thus, the laser module is more compact and efficient than current systems, which use a free space optical setup with multiple beam conversion in resonant cavities and collimation steps.

In general, according to one aspect, the invention features a scanning laser (and method of operation of a scanning laser) for producing patterned laser energy for an ophthalmic laser treatment system. The scanning laser comprises a laser module for producing laser energy, a scanning module for producing the patterned laser energy by deflecting the laser energy based on predetermined ophthalmic treatment patterns, and a delivery optics system for outputting the patterned laser energy to the ophthalmic laser treatment system.

In embodiments, the scanning module comprises one or more MEMS scanning mirrors (e.g. dielectric mirrors) or one or more galvanometers, the delivery optics system comprises an F-theta lens or a flat-field scanning lens, a focusing lens, and/or a spot-size selector module for adjusting spot sizes for the patterned laser energy. The scanning laser further comprises a fiber optic cable for directing the laser energy from the laser module to the scanning module.

Preferably, the laser module, the scanning module, and the delivery optics are enclosed within a compact assembly, and the ophthalmic laser treatment system is a slit-lamp laser treatment system or a laser indirect ophthalmoscope laser treatment system.

In general, according to another aspect, the invention features a system/method for delivering patterned laser energy to an eye of a patient. A control module sets parameters for the delivered patterned laser energy based on received parameter information and sends control signals based on the parameters. A scanning laser comprises a scanning module for producing the patterned laser energy by deflecting laser energy based on the control signals. The scanning laser receives the control signals from the control module and delivers the patterned laser energy based on the control signals.

In general, according to another aspect, the invention features an optical system for an ophthalmic laser treatment system. The optical system converts laser beams reflected from MEMS scanning mirrors at different scan angles into patterns in a plane.

Preferably, the optical system comprises an f-theta lens or a flat-field scanning lens.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. The patent or application file contains at least one drawing executed in color. Copies of this patent or patent application publication with color drawings(s) will be provided by the Office upon request and payment of the necessary fee. Of the drawings:

FIG. 4B is a perspective view of the pattern-scanning laser device with a portion of a housing of the device removed to reveal internal components;

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Figure 1:
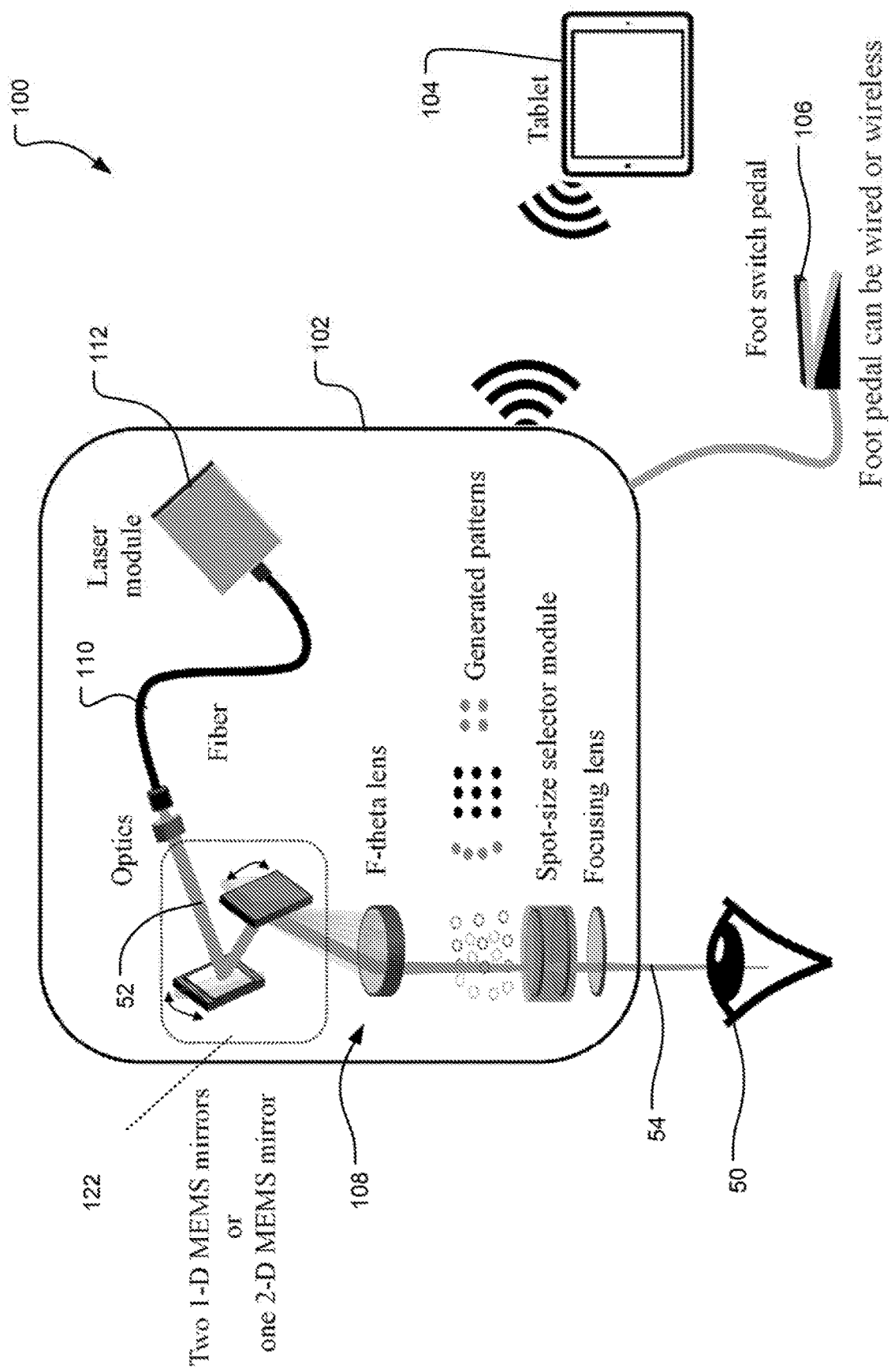
FIG. 1 is a schematic diagram of a laser treatment system according to the present invention.

FIG. 1 is a schematic diagram of a pattern-scanning laser treatment system 100 (e.g. for ophthalmology and adjacent sectors such as dermatology). In general, the pattern-scanning laser treatment system 100 delivers patterned laser energy 54 to an eye 50 (e.g. retina) or skin or other organ of a patient. The patterned laser energy 54 comprises one or more scanned laser beams arranged in a predetermined two-dimensional pattern of spots based on the pathology or treatment for the patient. In addition to delivering the patterned laser energy, the presently disclosed system can also deliver laser energy in a pulse train such as discrete pulses known as micropulses, each pulse having a duration ranging from 10-1000 microseconds (μs).

The laser treatment system 100 includes a pattern-scanning laser device 102, an activation unit 106 and a mobile computing device 104.

The pattern-scanning laser device 102 generates the patterned laser energy 54 and includes a laser module 112, a fiber optic cable or free space optical connection 110, a scanning module 122, and delivery optics 108.

The laser module 112 produces and emits laser energy according to certain user-provided parameters such as desired power, overall duration, and parameters related to pulsed laser energy including pulse envelope duration, peak power, and micropulse duration and interval, among other examples. The laser energy emitted by the laser module 112 is transmitted through the fiber optic cable 110 to the scanning module 122.

In the preferred embodiment, the laser module 112 produces laser energy suitable for ophthalmic treatments in a wavelength in the visible green or yellow wavelength range (e.g. 520-577 nm) with adjustable power output up to 1.2 Watts (W), with treatments typically being in the range of 0.1-1 W. A direct diode of the laser module produces a collimated beam, which is combined with a lower-power aiming beam (e.g. 1-5 mW) via a polarization or dichroic combiner and directed through optics for beam manipulation and shaping and into a 50-100 μm core fiber 110 to be delivered to the scanning module 122.

The scanning module 122 produces the patterned laser energy 54 by directing the laser energy 52 produced by the laser module into the delivery optics 108 at different angles according to pre-determined patterns of spots (e.g. each spot being associated with each reflected laser beam). The scanning module includes one or more scanning mirrors, preferably MEMS scanning mirrors, each comprising a reflective surface and associated control circuitry such as actuators, which cause the reflective surfaces of the mirrors to reflect incoming laser energy at different angles, for example, by tilting or rotating the mirrors about an axis. The reflective surface includes a reflective coating (e.g. highly reflective (HR) dielectric Bragg coatings for 520 nm wavelengths or external optical HR coatings).

In general, the dielectric mirrors have almost 100% reflectivity. This high reflectivity, typically greater than 95%, enables a more powerful laser and reduces heating of the mirror. Such heating can cause deformation of the mirror and thereby degrade the laser spot quality to an unacceptable level, when lower reflectivity mirrors are used.

Nevertheless, in other embodiments, aluminum or silver mirrors are used.

In the illustrated embodiment, the scanning module 122 includes two opposed one-dimensional scanning mirrors, the reflective surfaces of which each respectively rotate on a different axis. However, in other embodiments, the scanning module includes one two-dimensional scanning mirror, the reflective surface of which rotates on two different (e.g. mutually perpendicular) axes.

In another embodiment, the scanning module 122 includes galvanometers such as two sequential galvanometer (X & Y Axis) configurations, which generate a two-dimensional pattern by quickly steering the laser beam and automatically delivering all laser pulses in the selected pattern. In this example, the control module 414 includes a computer and galvanometer drivers to instruct the positioning of each galvanometer to the desired pattern display selected on the user interface.

The delivery optics 108 output the patterned laser energy to the patient's retina 50 (e.g. via a slit-lamp or LIO optics). In general, the delivery optics 108 are designed and configured to ensure beam quality and provide for adjusting the beam diameter via a motorized and wirelessly-controlled adjustment mechanism. In one example, the delivery optics 108 are designed to be capable of producing only specific laser beam spot sizes suitable for multi-spot ophthalmic laser treatments, such as spot sizes of 100 µm and 200 µm. In general, the delivery optics 108 are incapable of producing spots less than 40 µm or greater than 500 µm.

In the illustrated embodiment, the delivery optics 108 include an F-theta/scan lens, a spot size adjustment module, and a focusing lens. In an alternative embodiment, the delivery optics 108 includes a focusing lens.

The activation device 106, which is part of the user interface of the laser treatment system 100, is a device that receives user input via an activation mechanism (e.g. a switch or button) and in response sends activation signals to the scanning laser device 102 indicating that the laser energy should be emitted. The activation device 106 is typically a footswitch, and engagement with the activation mechanism includes compression of the footswitch by the user's foot, for example.

Preferably, the mobile computing device 104 is a medical device-grade tablet computer. Alternatively, the mobile computing device 104 could be a smartphone device, laptop computer, or phablet computer (i.e., a mobile device that is typically larger than a smart phone, but smaller than a tablet), to list a few examples. In general, the mobile computing device 104 provides additional components of the user interface and generates parameter information indicating the user-provided parameters based on input received via the user interface and wirelessly (e.g. via Bluetooth or Bluetooth Low Energy connectivity) sends the parameter information to the pattern-scanning laser device 102. The mobile computing device 104 includes a user interface including a graphical user interface and/or voice control capability. In examples, the mobile computing device 104 allows doctors to adjust power level, pulse duration, period, pre-set treatment programs, via touch or voice, and receive audible feedback indicating selected parameters.

Figure 2:
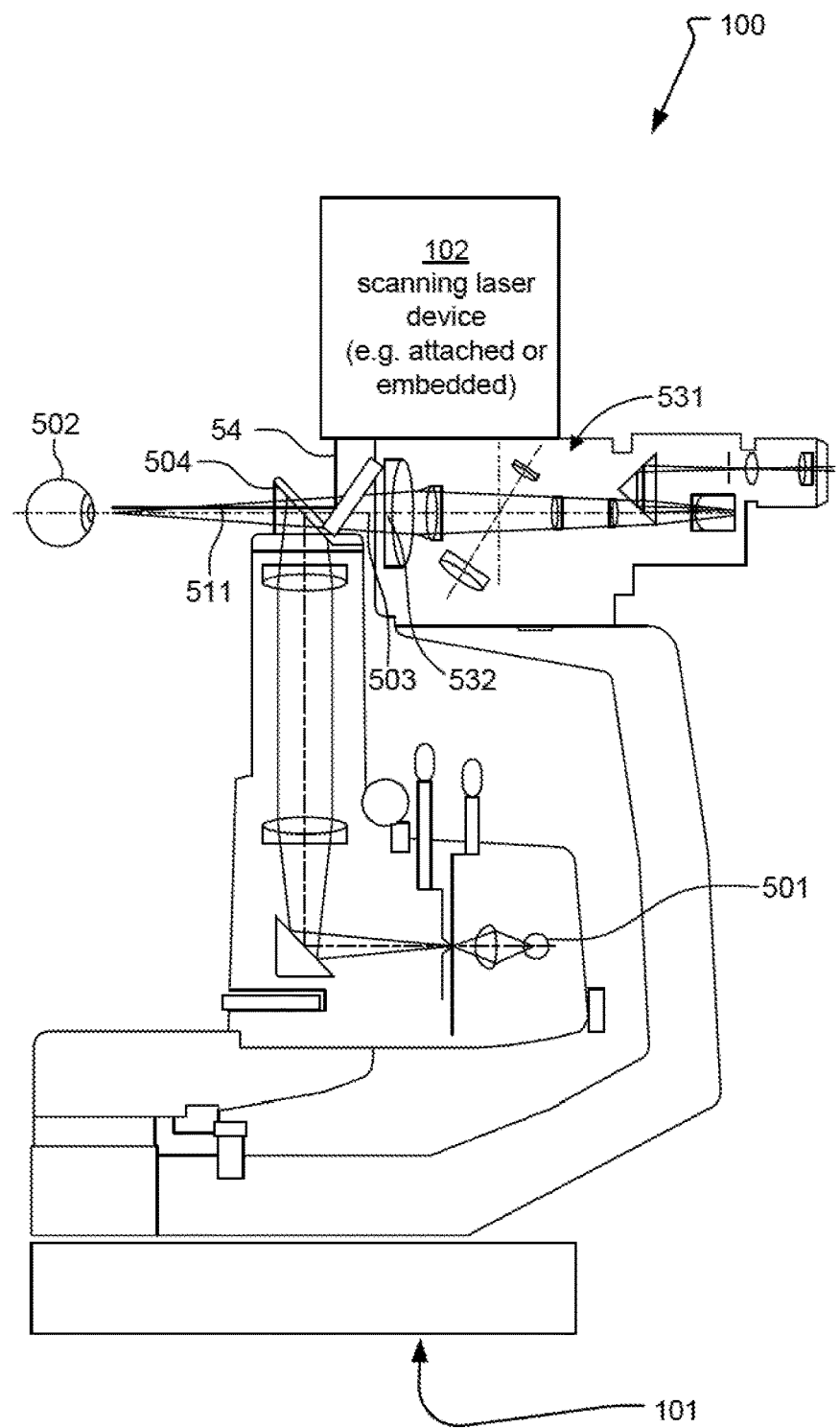
FIG. 2 is a schematic side view of the laser treatment system according to an embodiment in which a pattern-scanning laser device of the laser treatment system is attached to a slit lamp.

FIG. 2 schematically shows a slit lamp device 101 to which the present invention is applicable. The figure schematically shows the previously described pattern-scanning laser device 102 attached to or incorporated into the slit lamp 101. The slit lamp 101 includes a magnifying optical device 531, such as a microscope or zoom telescope, configured to receive light at a viewing input 532 along a viewing path 503 from a target area. The central part of the slit lamp 101 includes a white light source 501 that is used to illuminate a target area in the eye 502 of the patient. This white light is directed, by means of a mirror 504, onto an illumination output path 511 that coincides with the optical viewing path 503 of the operator at the designed focal point of the diagnostic instrument at the target area. In the same fashion, the light 54 from the laser is directed towards the target area along a treatment beam path such that it coincides with the viewing path, at least at the target area.

In one embodiment, the pattern-scanning laser device 102 is attached to an existing (e.g. legacy) slit lamp device 101 via an attachment mechanism. Preferably the light from the laser device 102 travels over a free space optical link from the device to the lamp 101, avoiding the need for an optical fiber connection.

In another embodiment, the pattern-scanning laser device 102 is fully integrated into the slit lamp device 102.

Figure 3:
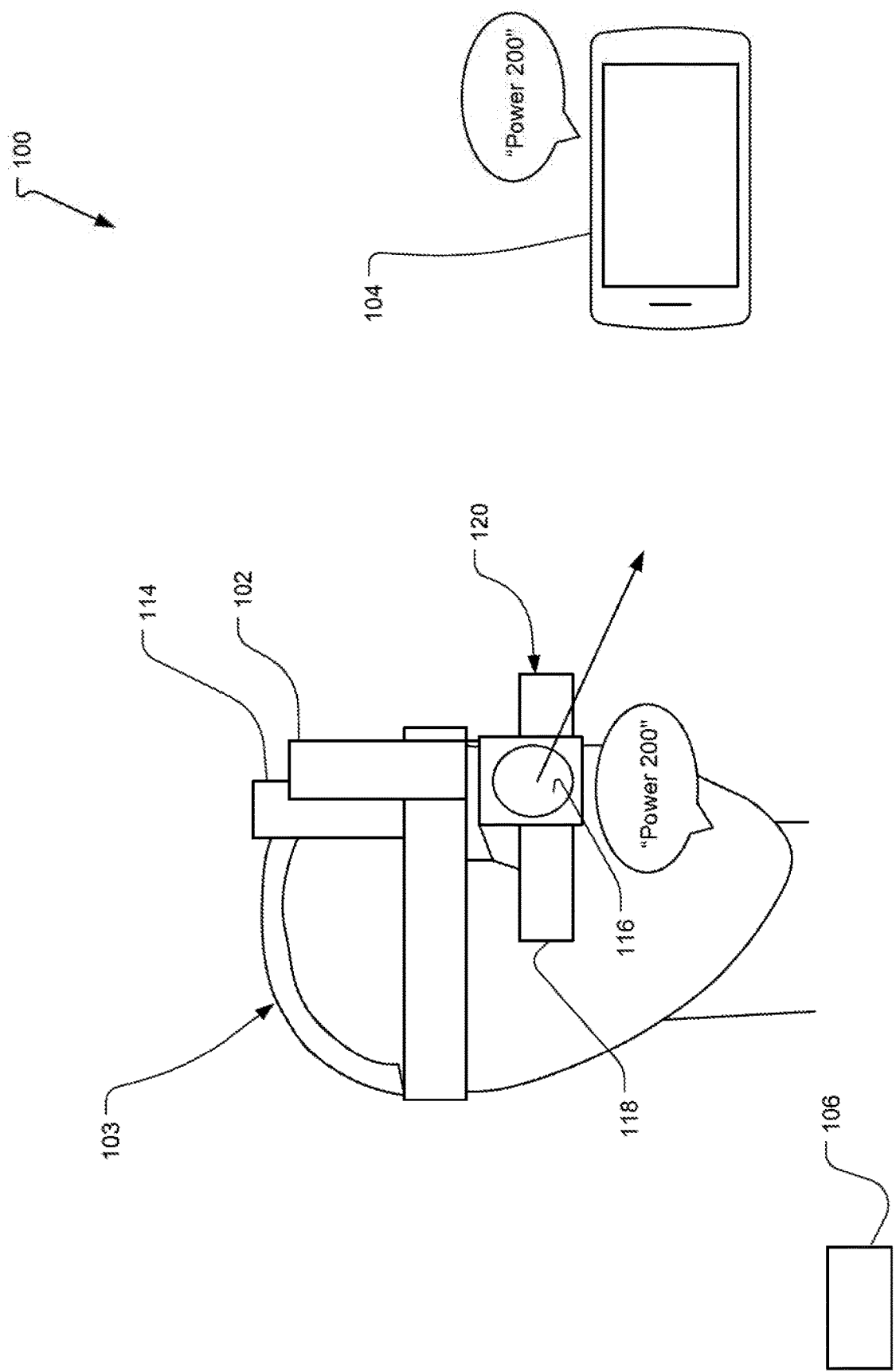
FIG. 3 is a schematic front view of the laser treatment system according to an embodiment in which the pattern-scanning laser device is attached to a body-mounted laser indirect ophthalmoscope.

FIG. 3 is an illustration of the laser treatment system 100 according to an embodiment in which the scanning laser device 102 is attached to a body-mounted LIO system. In general, the body-mounted LIO system delivers the patterned laser energy 54 to an eye 50 of a patient. A user of the LIO system is typically a doctor such as an ophthalmologist.

The body-mounted LIO system includes a binocular indirect ophthalmoscope 120, which is an optical device for examining the inside of the eye 50 of the patient. The binocular indirect ophthalmoscope 120 includes an illumination unit 114 for providing white light and an optical system including a viewing aperture 118 and an exit aperture 116 from which the laser energy is emitted (which is also an entrance aperture for image information e.g. for viewing the patient's eye).

The body-mounted LIO system includes a wearable assembly 103, which secures the body-mounted LIO system, including the pattern-scanning laser device 102, to the user's body via one or more wearable objects such as a headset, a utility belt, or a backpack, among other examples. In the illustrated example, the wearable assembly 103 comprises only a headset, which is worn on the user's head.

Figure 4A:
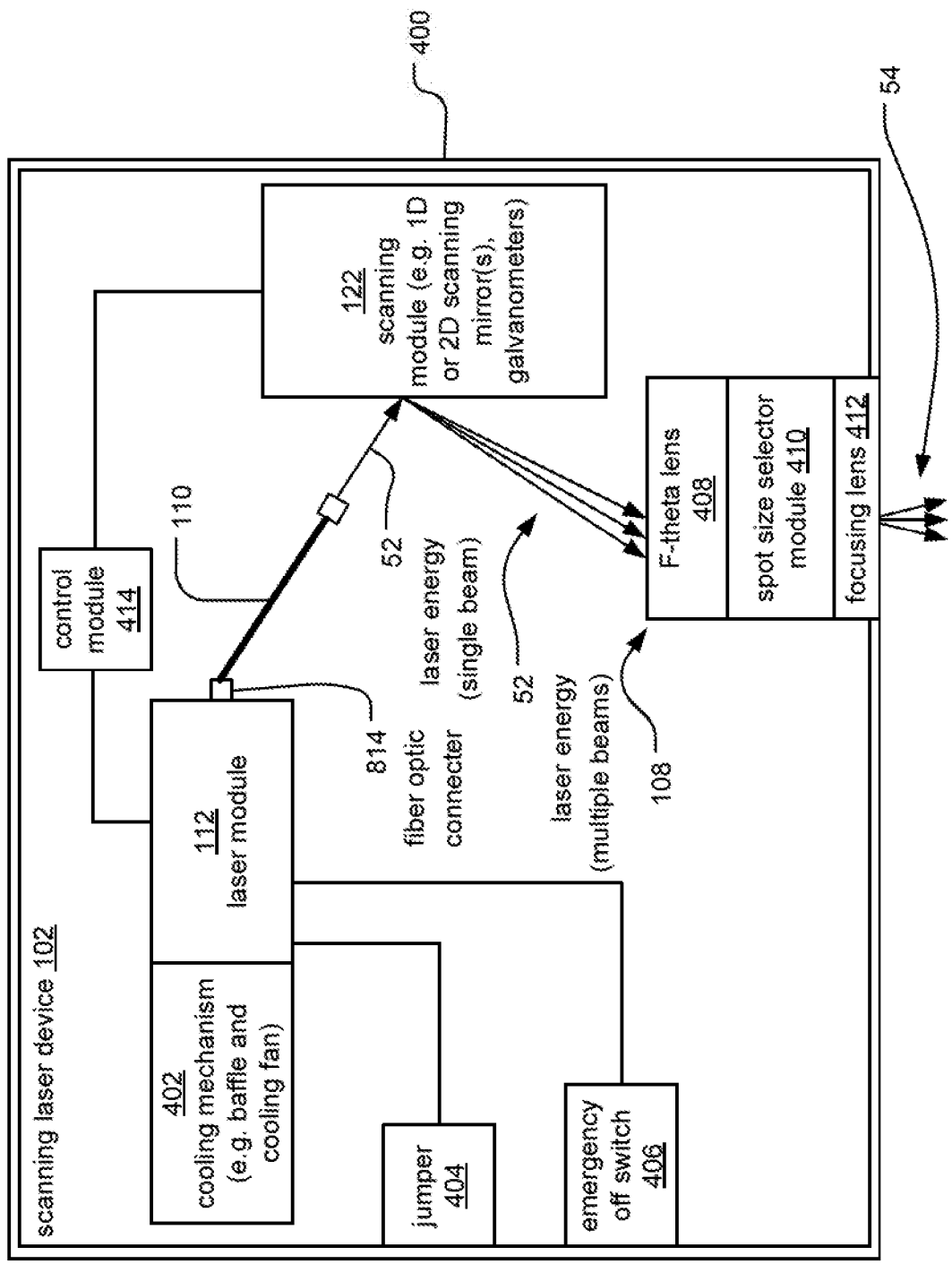
FIG. 4A is a schematic diagram of the pattern-scanning laser device.

FIG. 4A is a schematic diagram of the pattern-scanning laser device 102.

The pattern-scanning laser device 102 includes that laser module 112, fiber optic cable 110, scanning module 122, and delivery optics as previously described.

Now, however, additional components are shown, including a cooling mechanism 402, a jumper 404, an emergency off switch 406, a control module 414, an F-theta lens 408, spot size selector module 410, and focusing lens 412 of the delivery optics 108, and a compact housing 400.

The compact housing 400 provides an enclosure for all of the components of the scanning laser device 102, which is designed to have an optimal size, shape and weight based on the application of the pattern-scanning laser device 102. In one example, the compact housing 400 is designed to have an optimal size, shape and weight to be securely mounted to any existing slit-lamp or LIO using overhead space above the line of sight of the doctor and patient. In one example, the compact housing has a volume below 2 $dm^3$ (while the smallest system currently available is 29 $dm^3$) and a total weight (including all enclosed components of the device 102) of less than 2 kg.

The control module 414 controls the laser energy delivered by the laser module 112 based on parameter information received from the mobile computing device 104 and activation signals received from the activation device 106. In response to receiving the parameter information from the mobile computing device 104, the control module 414 sets the parameters for the laser energy to be emitted by the laser module 112 and for the patterns to be produced by the scanning module 122. In response to receiving activation signals from the activation device 106, the control module 414 sends control signals reflecting the user-provided parameters to the laser module 112 activating the laser module and causing it to produce and/or emit the laser energy and sends control signals to the scanning module 122 causing the scanning module 122 to reflect the laser energy 52 at different angles based on the selected pattern. In the illustrated example, the control module 414 is enclosed within the compact housing 400 of the pattern-scanning laser device 102. In other embodiments, the control module 414 is external to the housing 400 and sends control signals to the laser module 112 and scanning module 122 via a data port.

The cooling mechanism 402 is attached to the laser module 112 and includes a baffle to provide passive cooling of the laser module 112 and/or a cooling fan.

The jumper 404 and emergency off switch 406 are safety mechanisms that shut down the laser module 112 under certain conditions. The jumper 404 includes an interlock circuit that must be closed (e.g. with a key switched on and/or a connector plugged into a jack) for the laser module 112 to operate. The emergency off switch 406 shuts down the laser module 112 in response to activation of a switch mechanism (e.g. by a user).

The F-theta lens 408 converts laser beam reflected from the scanning module 122 at different scan angles into patterns of spots focused at a single plane by redirecting the beams so that they are displaced from each other (based on the scan angle) but parallel with respect to each other. In general, F-theta lenses are designed with a barrel distortion that yields a displacement that is linear with the angle with respect to the lenses' optical axis.

The spot size selector module 410 is an optical system comprising multiple lenses, which move (e.g. via a motor) with respect to each other in order to adjust the spot size for each beam of the patterned laser energy 54. In one example, the spot size selector module 410 wirelessly receives control signals (e.g. from the control module 414 or other control mechanism) and adjusts the spot sizes based on the control signals.

The focusing lens directs the patterned laser energy 54 onto a focal plane.

FIG. 4B is a perspective illustration of the pattern-scanning laser device 102 with a portion of the housing 400 cut away to reveal internal components.

The pattern-scanning laser device 102 includes that laser module 112, fiber optic cable 110 that ends with a collimation lens, scanning module 122, cooling mechanism 402, jumper 404, emergency off switch 406, control module 414, housing 400, and delivery optics 108, including the F-theta lens 408, spot size selector module 410, and focusing lens 412, as previously described.

Figure 5:
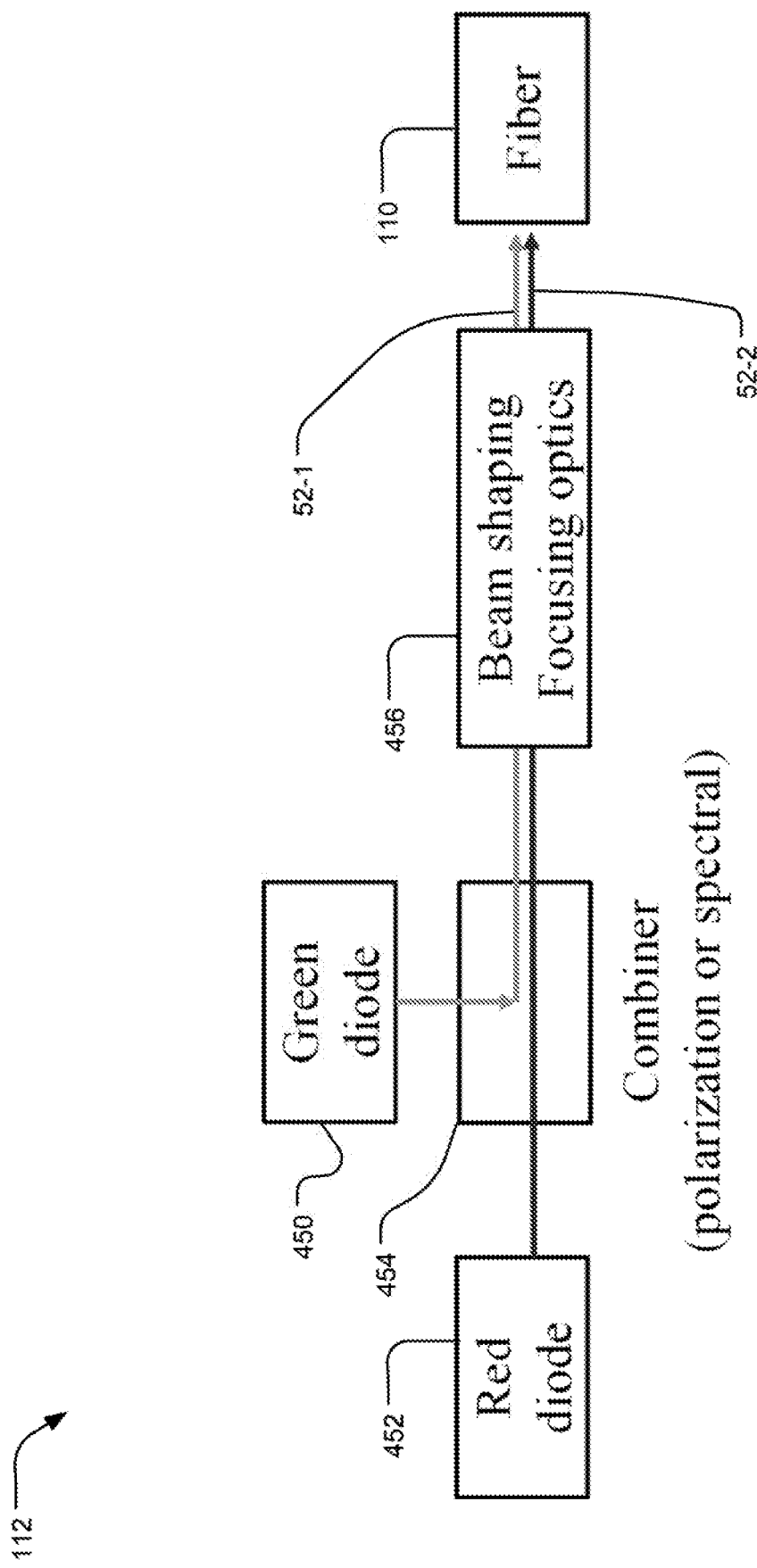
FIG. 5 is a block diagram of a laser module of the pattern-scanning laser device.

FIG. 5 is a schematic diagram of the laser module 112.

The laser module includes a green diode 450, a red diode 452, a combiner 454, and focusing lens 456.

The laser diodes 450, 452 produce laser energy (e.g. beams) of particular wavelengths (e.g. in the wavelength range of 495-580 nm associated with visible green and yellow light, or the wavelength range associated with visible red light for producing an aiming beam). The laser energy 52-1 produced by the green laser diode 450 and the laser energy 52-2 produced by the red laser diode 452 are combined by the polarization or spectral combiner (dichroic mirror) 454, which reflects one of the beams while transmitting the other, resulting in both propagating in the same direction. The combiner 454 directs the combined beam through the focusing lens 456 to the fiber optic cable 110 via a fiber optic connecter 814.

Figure 6:
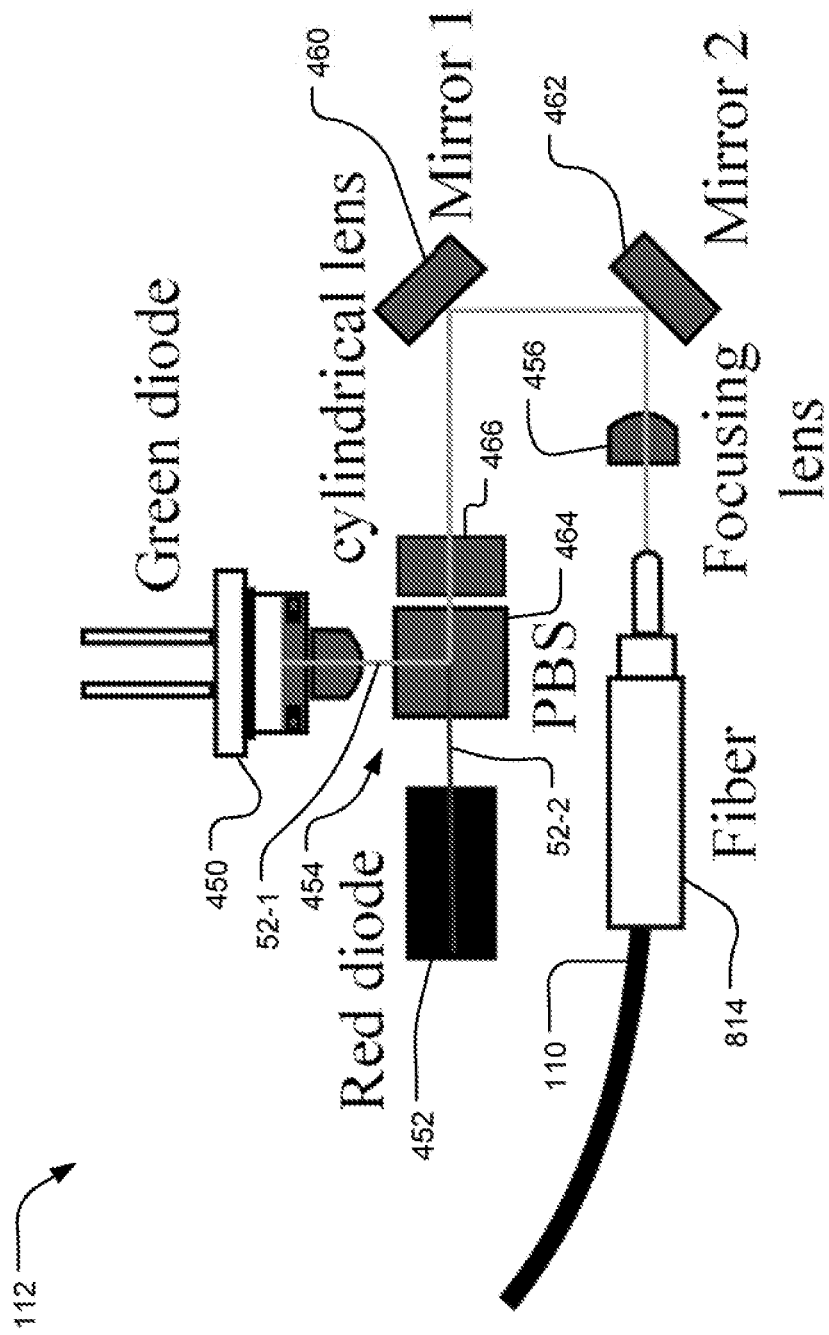
FIG. 6 is a schematic diagram of the laser module showing components in more detail.

FIG. 6 is a schematic diagram of the laser module 112 showing the components in more detail.

The laser module 112 includes the green diode 450, red diode 452, combiner 454, and focusing lens 456, as previously described.

Now, however, the components are shown in more detail, including a polarizing beam splitter 464 and a cylindrical lens 466 of the combiner 454, and a first mirror 460 and a second mirror 462, which provide optimal compactness.

In an alternative embodiment, a dichroic mirror is used in place of the polarization beam splitter 464.

The laser energy 52-1 produced by the green laser diode 450 and the laser energy 52-2 produced by the red laser diode 452 are combined by the polarizing beam splitter 464, which reflects one of the beams while transmitting the other, resulting in both propagating in the same direction. The polarizing beam splitter 464 directs the combined beam through the cylindrical lens 466 (e.g. part of a cylindrical telescope) to shape the beam. The first mirror 460 reflects the beam (e.g. at an angle of 90 degrees) to the second mirror 462, which reflects the beam (e.g. at an angle of 90 degrees) through the focusing lens 456 to the fiber optic cable 110 via the fiber optic connector 814.

This arrangement of the components of the laser module 112, including the two mirrors 460, 462 for redirecting the beam allows for a more compact design of the laser module 112.

Figure 7:
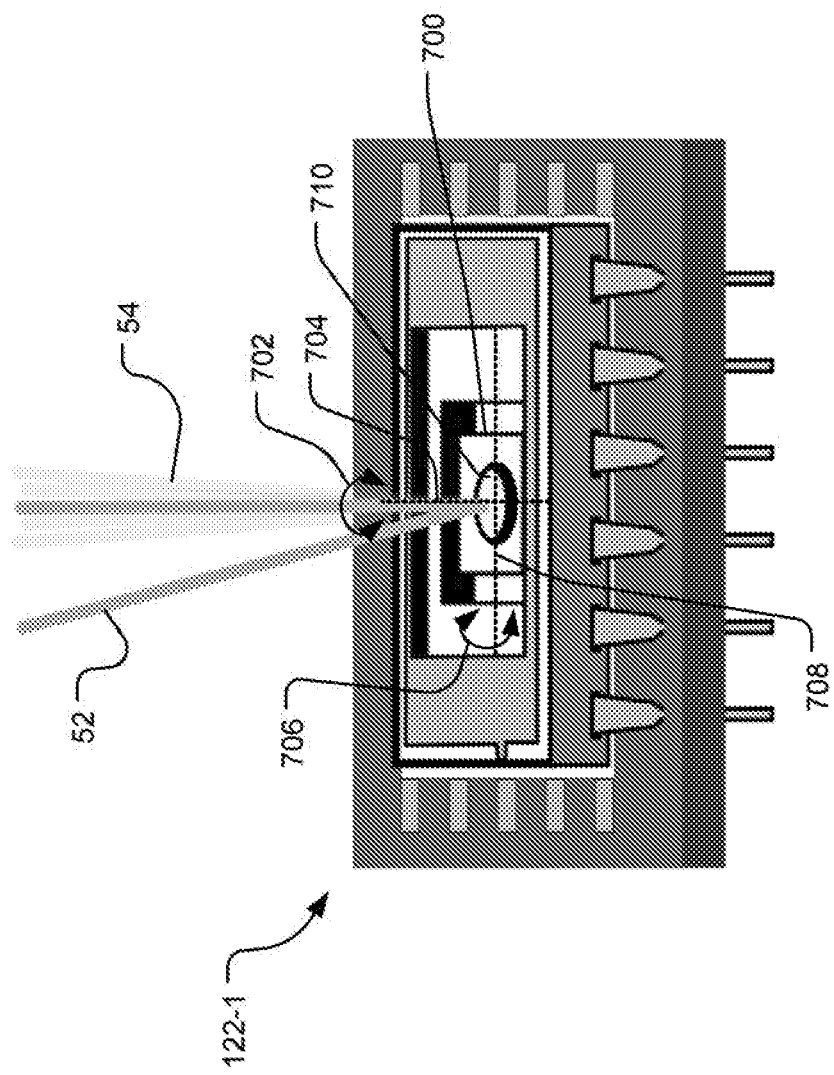
FIG. 7 is a perspective schematic view of an exemplary scanning module of the pattern-scanning laser device comprising a single two-dimensional scanning mirror.

FIG. 7 is a perspective view of an exemplary scanning module 122-1 comprising a single two-dimensional scanning mirror 700.

In general, the scanning module 122 is a microelectromechanical system (MEMS) microscanner containing a small mirror that has controllable tilt in one or two dimensions. It is housed within a dual inline pin (DIP) hermetic package that includes electrical pins and a transmissive window located over the mirror. The scanning module 122 may comprise position sensors (e.g. piezo resistive position sensors), actuators for moving the scanning mirror 700 (e.g. piezoelectric, electrostatic or magnetostrictive actuators) located behind the package's window and an integrated controller (e.g. microprocessor) for controlling the actuators based on data from the position sensors, which is integrated within the package. In one embodiment, however, the controller is implemented as a separate electronics board separate from the scanning mirror.

Having the position sensor integrated with the MEMS mirror 700 in a common package provides more accurate control of the mirror angle. Also, if the mirror suddenly fails (and that is a known risk of MEMS mirrors), the laser beam will not move and the current spot will receive much more laser energy than it should. This risk makes the position sensor an important safety feature of the MEMS scanner for ophthalmology applications.

In one embodiment, the scanning module 122 is a quasi-static or resonant two-dimensional MEMS scanner with vertical electrostatic comb drives and a MEMS fabrication process that is CMOS compatible.

In the illustrated example, the scanning mirror 700 rotates in a first direction 702 on a first axis 704 and also rotates in a second direction 706 on a second axis 708.

The scanning mirror comprises a reflective surface 710, which reflects incoming laser energy at different angles, for example, based on tilt of the mirror on each axis. The reflective surface 710 includes a reflective coating (e.g. HR Bragg dielectric coatings or metal coatings). In examples, the reflective coating reflects 520 nm and/or 635 nm wavelengths corresponding to the laser energy and/or an aiming beam.

In the preferred embodiment, the scanning mirror 700 is a dielectric Bragg mirror with a reflective surface 710 comprising multiple thin layers of dielectric material with specified reflectivity at different wavelengths such that the scanning mirror 700 reflects the laser energy 52 with an absorption rate that is low enough to preserve the integrity of the mirror and prevent overheating.

Figure 8:
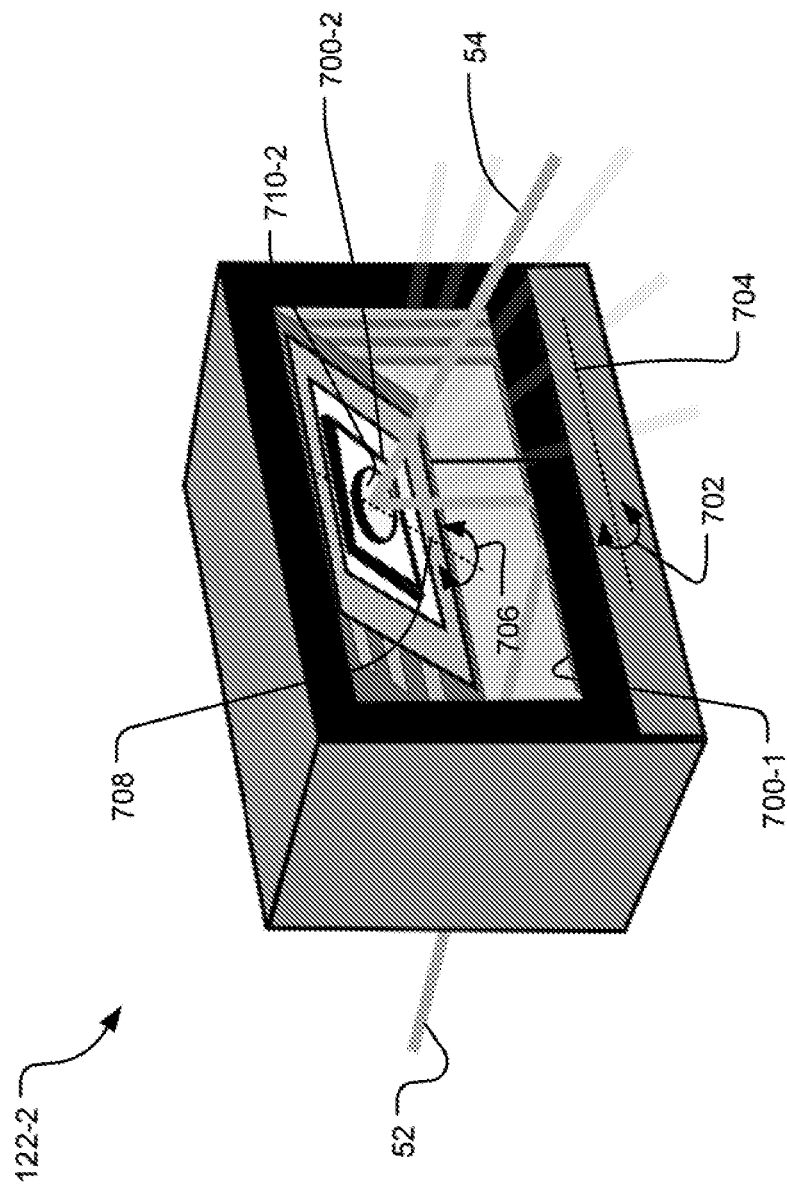
FIG. 8 is a perspective view of an exemplary scanning module comprising two one-dimensional scanning mirrors.

FIG. 8 is a perspective view of an exemplary scanning module 122-2 comprising two one-dimensional scanning mirrors 700.

The first scanning mirror 700-1 rotates in the first direction 702 around the first axis 704, reflecting light to the second scanning mirror 700-2, which rotates in the second direction 706 around the second axis 708.

Figure 9:
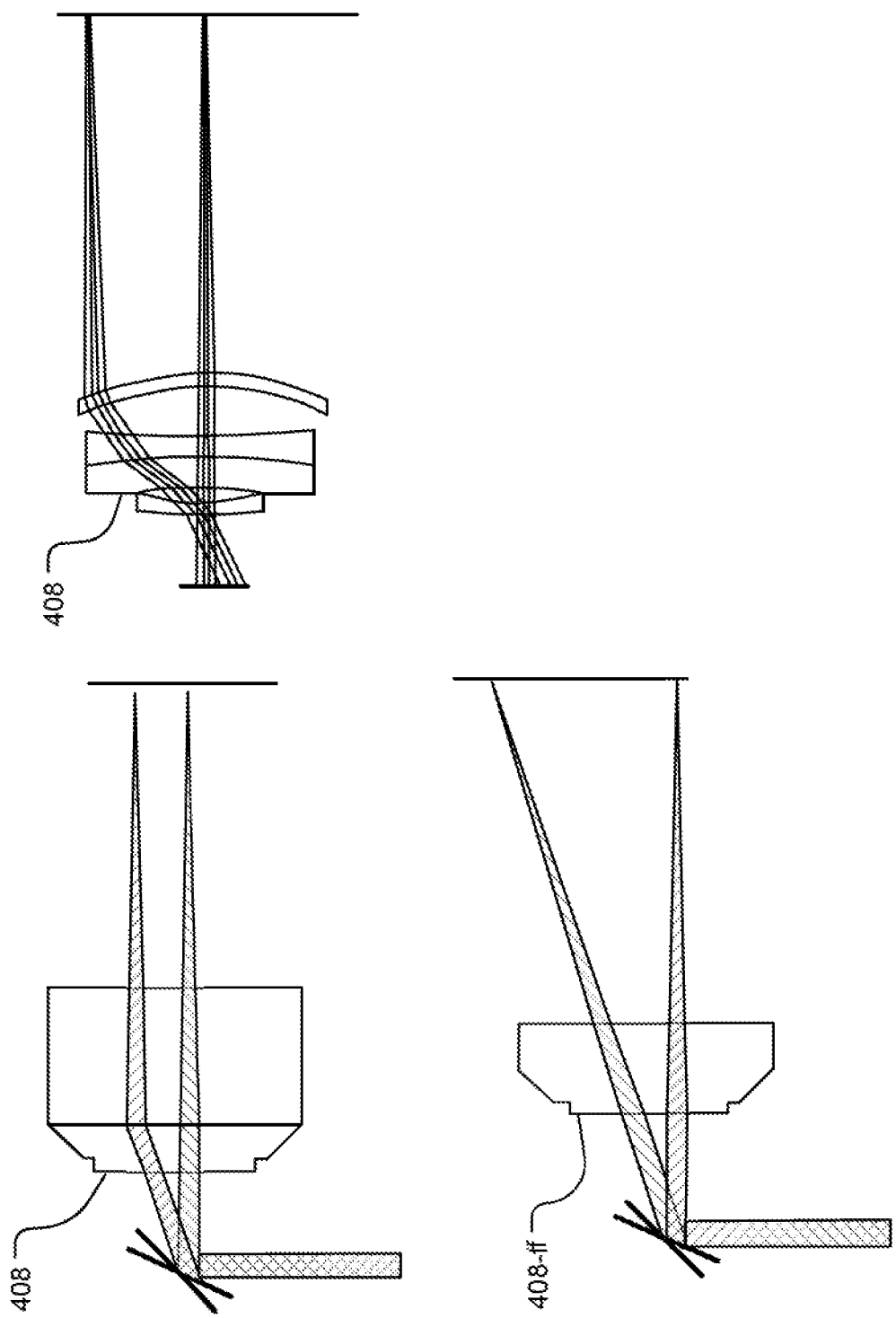
FIG. 9 is a side view showing an exemplary F-theta lens of delivery optics for the pattern-scanning laser device and an alternative flat-field scanning lens.

FIG. 9 is a side view showing an exemplary F-theta lens 408. The F-theta lens 408 converts incoming deflected laser beams such that the focal plane is a flat surface. In the illustrated example, the F-theta lens 408 is a telecentric lens, which is designed such that the incoming laser beams strike normal to the work surface (e.g. the surface of the eye 50 of the patient) over the entire scanning field. The F-theta lens 408 is the preferred solution/configuration, since the spot-to-spot distance remains constant at all distances. However, an alternative flat-field scanning lens 408-*ff* is also depicted.

Figure 10:
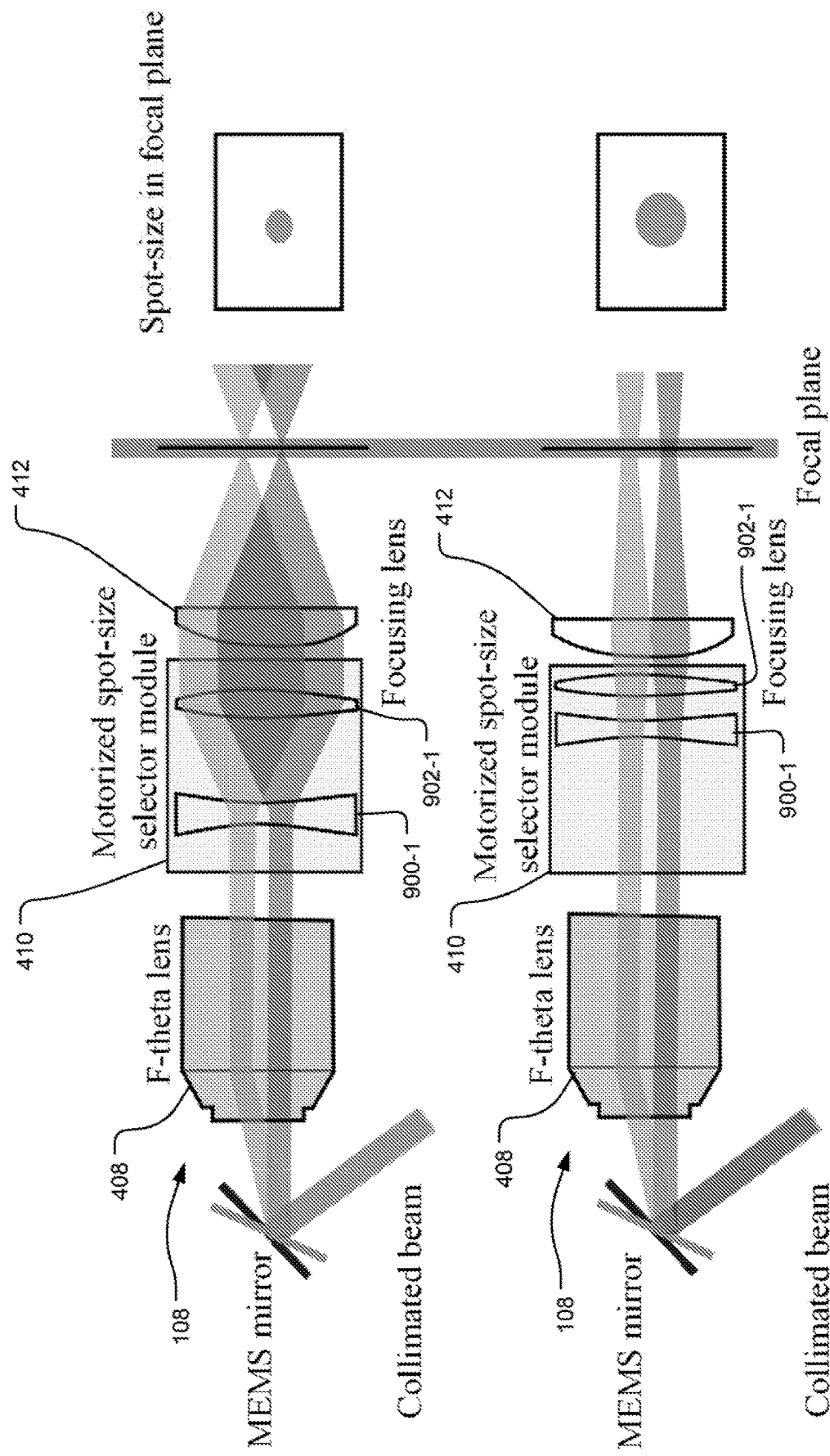
FIG. 10 is a side view of the delivery optics showing the F-theta lens, a spot-size selector module and a focusing lens.

FIG. 10 is a side view of the delivery optics 108, including the F-theta lens 408, the spot-size selector module 410 and the focusing lens 412.

The spot-size selector module 410 includes a first selector concave lens 900-1 and a second selector convex lens 900-2. The F-theta lens 408 directs the patterned laser energy 54 first through the first selector lens 900-1 and then through the second selector lens 900-2 into the focusing planoconvex lens 412. The spot size is based on the positions of the selector lenses 900, 902.

In the top example, the first selector lens 900-1 is relatively far from the second selector lens 902-1, resulting in a relatively small spot size.

In the bottom example, the first selector lens 900-2 is relatively close to the second selector lens 902-2, resulting in a relatively larger spot size.

The spot-size selector module 410 operates by moving the first selector lens 900-1 along the lens system axis at varying distances from the second selector lens 900-2 based on the desired spot size. This movement is provided, for example, via a motorized movement mechanism which is wirelessly controlled.

Figure 11:
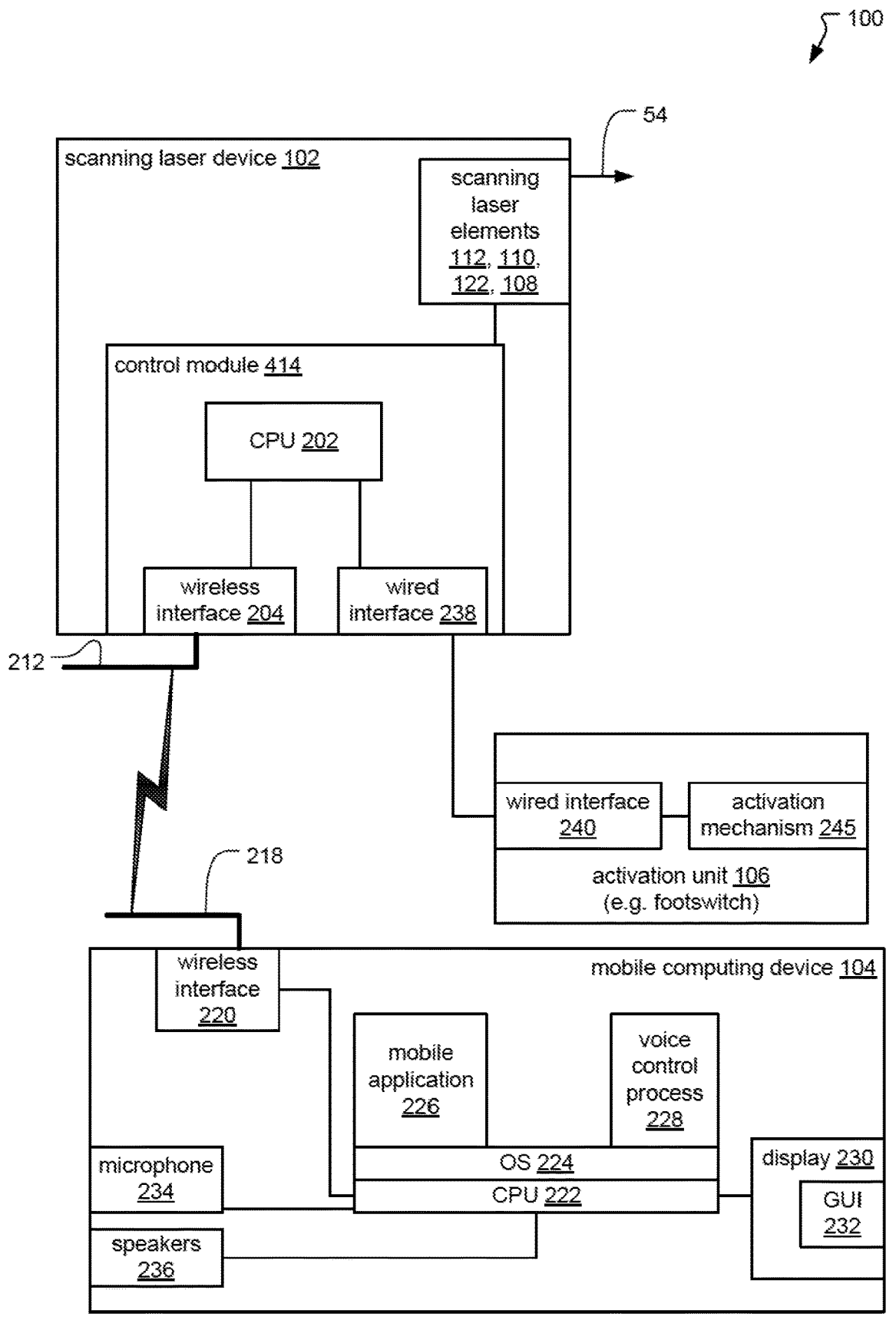
FIG. 11 is a schematic diagram of the laser treatment system showing components of the pattern-scanning laser device, an activation unit and a mobile computing device.

FIG. 11 is a schematic diagram of the laser treatment system 100 showing components of the scanning laser device 102, activation unit 106 and mobile computing device 104 in more detail.

The scanning laser device 102 includes the scanning laser elements 112, 110, 122, 108 and control module 414 as previously described.

Now, however, internal components of the control module 414 are shown.

The control module 414 includes a CPU 202, a wireless interface 204 and a wired interface 238. The CPU 202 directs the functionality of the control module 108 such as receiving parameter information from the mobile computing device 104 and activation signals from the activation device 106 via the wireless interface 204 and antenna 212 and the wired interface 238, as well as sending control signals to the laser module 112, the scanning module 122 and/or the spot-size selector module 410.

The mobile computing device 104 includes a central processing unit (CPU) 222, a touchscreen display 230, a wireless interface 220 and antenna 218, a microphone 234 and speakers 236.

The CPU 222 executes firmware/operating system instructions and sends instructions and data to and receives data from the wireless interface 220, the microphone 234, the speakers 236, and the display 230. Executing on typically an operating system (OS) 224 of the CPU 222 are a mobile application 226 and a voice control module 228. The mobile application 226 renders a graphical user interface (GUI) 232 on the touchscreen display 230. The GUI 232, which is part of the user interface of the laser treatment system 100, is optimized to each treatment protocol and presents parameter information including stored preset treatment parameters for most used treatments, data from recent treatments, and/or a user manual, among other examples. The GUI 232 also receives parameter information, for example, by detecting contact between the user and the touchscreen display 230 in certain regions of the touchscreen display 230. The mobile application 226 also performs functions related to configuring the laser treatment system 100 such as pairing the mobile computing device 104 with the control module 414 and/or setting a wake word, which is a selected phrase for indicating that verbal commands follow.

The microphone 234 captures sound including the wake word and voice commands indicating parameter information provided by the user, which the mobile computing device 104 converts to audio data.

The speakers 236 produce sound based on instructions from the parameter regulation module 229, for example, in order to provide audible feedback confirming parameter information and/or voice commands.

In general, the voice control module 228 provides voice control capability, including internet-free connectivity and an expandable, customized library of multilingual commands. The voice control module 228 generates voice command information based on the captured audio data. In one example, the voice control module 228 recognizes spoken language in the audio data and translates the spoken language to commands that can be interpreted and/or executed by the control module 414.

In the illustrated example, the voice control module 228, microphone 234, speakers 236, GUI 232 rendered on the touchscreen display 230, and the activation device 106 provide a general user interface (UI) for the laser treatment system 100. However, in other embodiments (not illustrated) the UI for the laser treatment system 100 can also include other user interface elements such as physical input mechanisms such as knobs or buttons, which can be part of the mobile computing device 104 itself or part of peripheral devices connected to the mobile computing device 104 via the wireless interface 220 and/or a physical interface (e.g. data port). In general, the parameter information can be generated by the mobile computing device 104 based on any user engagement with the mobile computing device 104 and/or peripheral devices.

The wireless network interface 220 facilitates sending the parameter information to the control module 108 via the antenna 218 through a wireless communication link with the control module 108 according to wireless personal area network (WPAN) or wireless local area network (WLAN) protocols such as Bluetooth Low Energy (BLE) or WiFi, among other examples.

Finally, the activation unit 106 receives user input via an activation mechanism 245 (e.g. a switch or button) and in response to the user input, the activation unit 106 generates and sends activation signals to the control module 108 and/or to the mobile computing device 104, based on the configuration of the laser treatment system 100, via a wired interface 240. In the preferred embodiment, the activation unit 106 is a footswitch, and engagement with the activation mechanism 245 includes compression of the footswitch by the user's foot, for example.

Figure 12:
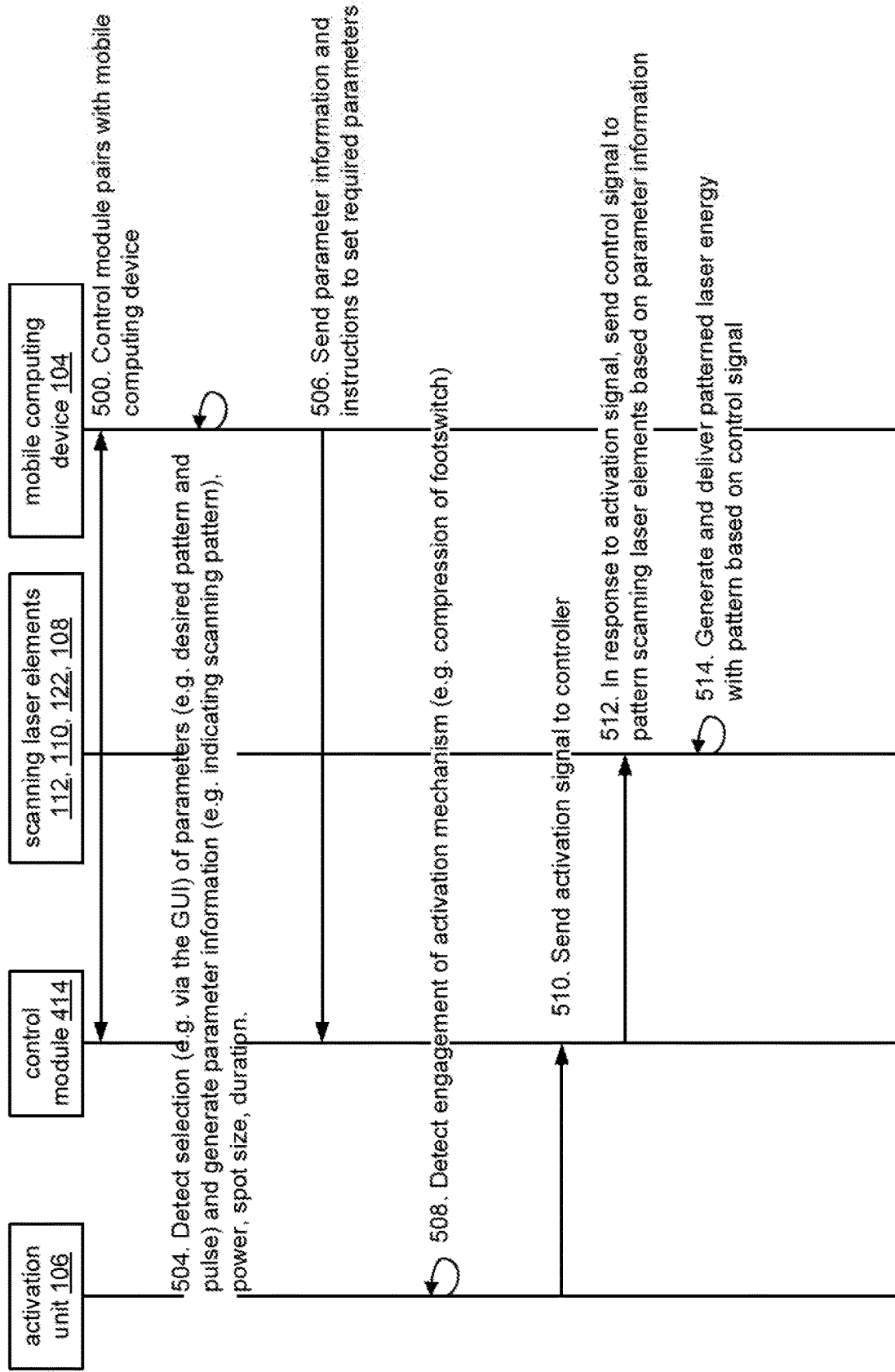
FIG. 12 is a sequence diagram illustrating the process by which the laser treatment system delivers patterned laser energy to an eye of a patient.

FIG. 12 is a sequence diagram illustrating the process by which the laser treatment system 100 delivers the patterned laser energy 54 to the eye 50 of the patient.

First, in step 500, the control module 414 pairs with the mobile computing device 104 by, for example, establishing a wireless communication link and/or exchanging identification information for the two devices, among other examples.

In step 504, the mobile computing device 104 detects input via the GUI 232 or the UI in general and generates parameter information based on the input. In one example, the doctor selects a virtual button indicating the power parameter or enters via a virtual keyboard a numerical value indicating the desire power setting (e.g. 200). In another example, the doctor adjusts a dial or increment button indicating the desired power setting (e.g. 200). In another example, the doctor speaks a desired power setting. In yet another example, the doctor indicates the desired pattern via the GUI 232 by selecting from a set of pre-determined patterns and/or by indicating where each spot in the pattern should be relative to the others, among other examples.

In step 506, the mobile computing device 104 sends the parameter information to the control module 414 along with instructions to set the required parameters based on the parameter information, and the parameters are updated.

In step 508, the activation unit 106 detects engagement of the activation mechanism 245. In one example, the user's foot compresses a footswitch. In response, in step 510, the activation unit 106 sends an activation signal to the control module 414.

In response to receiving the activation signal, the control module 414 in step 512 sends control signals to the pattern scanning laser elements, including the laser module 112, the scanning module 122, and/or the spot-size selector module 410. In one example, the control module 414 sends control signals to the laser module 112 indicating that the laser energy should be generated with a certain power level based on the parameter information. In another example, the control module 414 sends control signals to the scanning module 122 indicating that the scanning mirror(s) 900 should be tilted in a particular sequence (e.g. of tilt angles) based on a desired pattern indicated in the parameter information. In yet another example, the control module 414 sends control signals to the spot-size selector module 410 indicating adjustment of the spot size of the laser beams to a particular size based on the parameter information.

In step 514, in response to receiving the control signals, the scanning laser elements generate and deliver the patterned laser energy based on the control signals and the parameter information. For example, in response to receiving the control signals, the laser module 112 produces laser energy with a power and pulse sequence based on the control signals. In another example, in response to receiving the control signals, the scanning module 122 tilts the scanning mirror(s) 900 in order to reflect the laser energy 52 to the delivery optics 108 at different angles based on a predetermined pattern indicated by the control signals. In yet another example, the spot size selector module 410, in response to receiving the control signals, adjusts the spot size (e.g. by adjusting the positions of the first and second selector lenses 900, 902 relative to each other).

While this invention has been particularly shown and described with references to preferred embodiments thereof, it will be understood by those skilled in the art that various changes in form and details may be made therein without departing from the scope of the invention encompassed by the appended claims.

For example, the galvanometers or MEMS mirror could be replaced with a lens that is moved by small electromagnets (as used in digital camera image stabilizers).

Still another solution could be the combination of a 1D MEMS scanner and an alternative technology for the other scanning axis. The advantage is that the speed requirement for the other axis is lower. Therefore a slower scanning technology is acceptable for that scan axis. Such a slower scanner could be: moving fiber bundle, moving cylindrical lens, or a galvanometer.

What is claimed is:

1. A scanning laser for producing patterned laser energy for an ophthalmic laser treatment system, the scanning laser comprising:
    a laser module for producing laser energy;
    a scanning module for producing the patterned laser energy by deflecting the laser energy based on predetermined ophthalmic treatment patterns;
    a delivery optics system including:
        a lens that receives the patterned laser energy at different angles from the scanning module, and
        a spot size selector module for adjusting spot sizes for the patterned laser energy received from the scanning module and the lens, the delivery optics outputting the patterned laser energy to the ophthalmic laser treatment system; and
    a housing, mounted on the ophthalmic laser treatment system, containing the laser module, the scanning module, and the delivery optics;
    wherein the patterned laser energy travels from the scanning module to the ophthalmic laser treatment system via a free space path with no optical fiber connection.

2. The scanning laser of claim 1, wherein the scanning module comprises one or more MEMS scanning mirrors and/or moving lenses and/or 1D MEMS scanning mirrors and an alternative technology for the other scanning axis, such as moving fiber bundle, moving cylindrical lens, and/or galvanometer and/or other technology.

3. The scanning laser of claim 1, wherein the scanning module comprises one or more MEMS dielectric scanning mirrors.

4. The scanning laser of claim 1, wherein the scanning module comprises one or more galvanometers.

5. The scanning laser of claim 1, wherein the lens of the delivery optics system is an F-theta lens.

6. The scanning laser of claim 1, wherein the lens of the delivery optics system is a flat-field scanning lens.

7. The scanning laser of claim 1, wherein the delivery optics system further comprises a focusing lens.

8. The scanning laser of claim 1, wherein the laser module, the scanning module, and the delivery optics are enclosed within a compact assembly.

9. The scanning laser of claim 1, wherein the ophthalmic laser treatment system is a slit-lamp laser treatment system.

10. The scanning laser of claim 1, further comprising a position sensor integrated with the scanning module, which position sensor is optionally employed as a safety feature in case of module failure.

11. The scanning laser of claim 1, wherein the patterned laser energy travels from the scanning module to the delivery optics via a free space path.

12. The scanning laser of claim 1, wherein the spot size selector module comprises multiple lenses and a motor for moving the lenses relative to each other in order to adjust a spot size of the patterned laser energy.

13. The scanning laser of claim 12, wherein the multiple lenses of the spot size selector module include a selector concave lens and a selector convex lens.

14. A scanning laser for producing patterned laser energy for an ophthalmic laser treatment system, the scanning laser comprising:
- a laser module for producing laser energy;
- a scanning module for producing the patterned laser energy by deflecting the laser energy based on predetermined ophthalmic treatment patterns; and
- a delivery optics system outputting the patterned laser energy to the ophthalmic laser treatment system, wherein the delivery optics include:
  - a lens that receives the patterned laser energy at different angles from the scanning module, and
  - a spot size selector module for adjusting spot sizes for the patterned laser energy received from the scanning module and the lens; and
- a housing, mounted on the ophthalmic laser treatment system, containing the laser module, the scanning module, and the delivery optics system;
- wherein the patterned laser energy travels from the scanning laser to the ophthalmic laser treatment system via a free space path with no optical fiber connection.

* * * * *